(12) United States Patent
Becker et al.

(10) Patent No.: US 7,731,694 B2
(45) Date of Patent: Jun. 8, 2010

(54) HEMOSTASIS SEAL

(75) Inventors: Neil M. Becker, Fallbrook, CA (US); Christopher C. Andrews, Lake Elsinore, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 531 days.

(21) Appl. No.: 11/257,201

(22) Filed: Oct. 24, 2005

(65) Prior Publication Data

US 2007/0106262 A1      May 10, 2007

(51) Int. Cl.
*A61M 5/178* (2006.01)
*A61B 17/34* (2006.01)

(52) U.S. Cl. .................... 604/167.06; 606/185

(58) Field of Classification Search ............. 604/34, 604/104, 161–163, 165, 166, 167, 167.01–167.09, 604/169–171, 237, 247, 256, 264; 606/167, 606/185; 251/149.1, 149.2; 137/849, 855
See application file for complete search history.

(56) References Cited

U.S. PATENT DOCUMENTS

| | | | |
|---|---|---|---|
| 3,113,586 A * | 12/1963 | Edmark, Jr. ............. 137/512.1 |
| 4,655,752 A | 4/1987 | Honkanen et al. |
| 4,747,840 A * | 5/1988 | Ladika et al. .............. 604/532 |
| 4,798,594 A | 1/1989 | Hillstead |
| 4,895,346 A | 1/1990 | Steigerwald |
| 4,895,565 A | 1/1990 | Hillstead |
| 4,909,798 A | 3/1990 | Fleischhacker et al. |
| 4,917,668 A | 4/1990 | Haindl |
| 4,929,235 A | 5/1990 | Merry et al. |
| 5,000,745 A | 3/1991 | Guest et al. |
| 5,114,408 A | 5/1992 | Fleischhaker et al. |
| 5,125,903 A | 6/1992 | McLaughlin et al. |
| 5,149,327 A | 9/1992 | Oshiyama |
| 5,167,637 A | 12/1992 | Okada et al. |
| 5,330,437 A * | 7/1994 | Durman ................. 604/167.04 |
| 5,385,552 A | 1/1995 | Haber et al. |
| 5,520,655 A | 5/1996 | Davila et al. |
| 5,643,227 A | 7/1997 | Stevens |
| 5,693,025 A | 12/1997 | Stevens |
| 5,743,884 A | 4/1998 | Hasson et al. |
| 5,935,112 A | 8/1999 | Stevens et al. |
| 6,083,207 A * | 7/2000 | Heck ...................... 604/256 |
| 6,086,570 A | 7/2000 | Aboul-Hosn et al. |

(Continued)

OTHER PUBLICATIONS

International Search Report and Written Opinion of International Application No. PCT/US2006/060159, filed Oct. 23, 2006, both mailed Jun. 18, 2007.

*Primary Examiner*—Kevin C Sirmons
*Assistant Examiner*—William Carpenter
(74) *Attorney, Agent, or Firm*—Faegre & Benson LLP

(57) ABSTRACT

A hemostasis seal configured for use in a splittable hemostasis valve, hub, or introducer sheath to permit passage of a medical device therethrough. The seal provides a substantially fluid-tight seal around the medical device without causing excessive frictional resistance that would otherwise unduly restrict movement of the medical device through the seal. In one embodiment, the seal includes first and second resilient seal portions each having a contoured mating surface to provide a first fluid seal with respect to the medical device. The seal also may include one or more projecting portions and one or more mating receiving portions which interact to provide a second fluid seal with respect to the medical device.

15 Claims, 8 Drawing Sheets

U.S. PATENT DOCUMENTS

| | | | |
|---|---|---|---|
| 6,142,981 A | 11/2000 | Heck et al. | |
| 6,238,373 B1 | 5/2001 | de la Torre et al. | |
| 6,331,176 B1 | 12/2001 | Becker et al. | |
| 6,551,283 B1 * | 4/2003 | Guo et al. | 604/167.06 |
| 6,602,240 B2 | 8/2003 | Hermann et al. | |
| 6,623,460 B1 | 9/2003 | Heck | |
| 6,632,200 B2 | 10/2003 | Guo et al. | |
| 6,634,364 B2 | 10/2003 | Westlund et al. | |
| 6,702,255 B2 | 3/2004 | Dehdashtian | |
| 6,702,828 B2 | 3/2004 | Whayne | |
| 6,723,073 B2 | 4/2004 | Ley et al. | |
| 2002/0010425 A1 * | 1/2002 | Guo et al. | 604/167.04 |
| 2002/0072712 A1 | 6/2002 | Nool et al. | |
| 2002/0077683 A1 | 6/2002 | Westlund et al. | |
| 2003/0085373 A1 | 5/2003 | Dehdashtian | |
| 2004/0049158 A1 | 3/2004 | Ley et al. | |
| 2004/0210194 A1 | 10/2004 | Bonnette et al. | |
| 2004/0267202 A1 | 12/2004 | Potter | |
| 2005/0020981 A1 | 1/2005 | Kurth | |
| 2005/0033239 A1 | 2/2005 | Argentine | |
| 2005/0228346 A1 | 10/2005 | Goode et al. | |
| 2006/0030825 A1 * | 2/2006 | Enns et al. | 604/264 |
| 2006/0135972 A1 * | 6/2006 | Zeiner | 606/167 |
| 2006/0135977 A1 * | 6/2006 | Thompson et al. | 606/185 |

* cited by examiner

HEMOSTASIS SEAL

TECHNICAL FIELD

The present invention relates generally to the field of medical instruments, and more particularly to hemostasis seals for use during medical procedures.

BACKGROUND

Various medical procedures require the introduction of one or more medical instruments into arteries or veins so that the medical instruments may be advanced to a body location requiring diagnosis or treatment. For example, a guide catheter may be advanced through the patient's vasculature to a desired treatment location, such as the right atrium of the patient's heart, for delivery of a cardiac lead. A mechanism (e.g., a hemostasis valve) including a hemostasis seal may be located at the proximal end of the guide catheter to control or inhibit the flow of blood out of the guide catheter lumen. A cardiac lead or other device (e.g., a guide wire) may be inserted through the seal and the guide catheter lumen and into the patient's vasculature, and the seal inhibits blood flow around the lead.

The seal should accommodate medical devices (e.g., leads, catheters and guide wires) of varying diameters without unduly restricting the movement of the device, yet still effectively seal against the flow of bodily fluids. In addition, the seal may advantageously be designed to be splittable to facilitate removal of the guide catheter while leaving the inner medical device (e.g., guide wire or lead) in place in the patient's body.

Accordingly, there is a need for a splittable or cuttable hemostasis seal which effectively seals against leakage of bodily fluids without unduly resisting the insertion and retraction of elongated cylindrical medical devices of varying diameters.

SUMMARY

The present invention, according to one embodiment, is a hemostasis seal configured to permit passage of a medical device. The seal includes a first resilient seal portion having a first proximal seal member with a first mating surface, a first projecting portion, and a first receiving portion. The seal also includes a second resilient seal portion having a second proximal seal portion with a second mating surface, a second projecting portion, and a second receiving portion. The first mating surface is configured to mate with the second mating surface to form a first fluid seal with respect to the medical device. In addition, the first and second projecting portions are adapted to mate with and sealingly engage the second and first receiving portions, respectively, to form a second fluid seal with respect to the medical device.

In another embodiment, the present invention is a hemostasis seal configured to permit passage of a medical device, and includes a first resilient seal portion with a first mating surface that includes a projecting portion; and a second resilient seal portion with a second mating surface configured to mate with the first mating surface. The second mating surface includes a receiving portion adapted to mate with the projecting portion. The seal is configured such that the first and second seal portions seal around substantially the entire circumferential surface of the medical device when it is passed between the first and second seal portions.

The present invention, in yet another embodiment, is a hemostasis seal configured to permit passage of a medical device. The seal includes a pair of mating seal portions each having a proximal sealing member, a distal projecting member, and a distal receiving portion. The distal receiving portion of each seal portion is sized and shaped to sealingly receive the projecting member of the mating seal portion, and the proximal sealing members and the distal projecting members are configured to sealingly and slidably engage the medical device about substantially an entire circumferential surface thereof when the medical device is passed through the seal.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
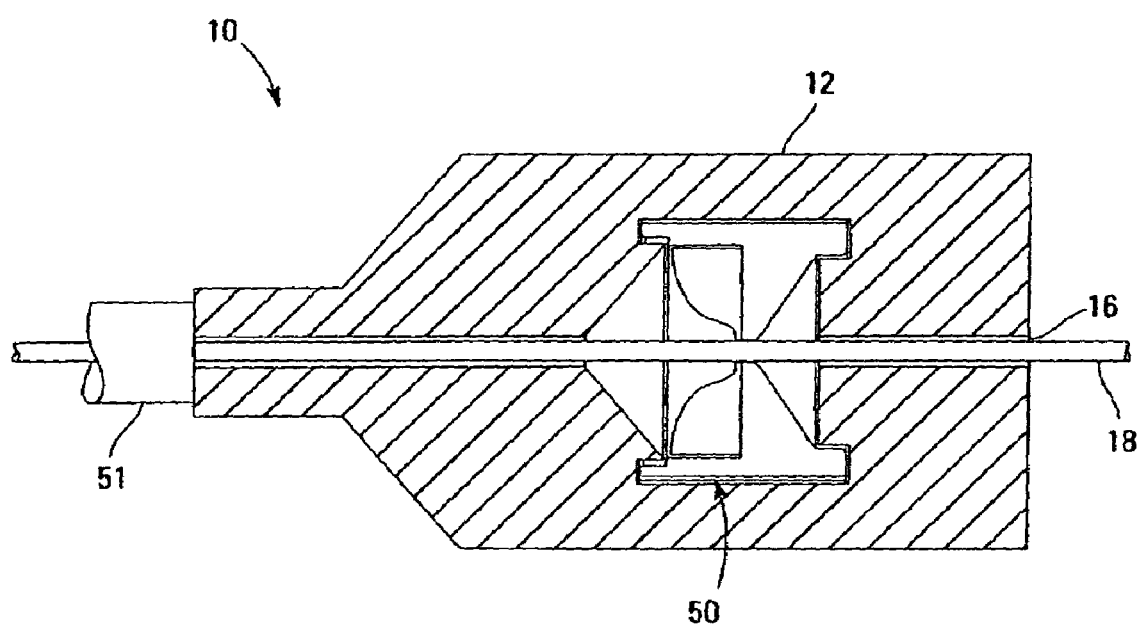
FIG. 1 is a schematic cutaway view of a hub assembly for use in a medical procedure, such as a catheterization procedure, according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 depicts, schematically, a hub assembly 10 for use in a medical procedure, such as a catheterization procedure, according to one embodiment of the present invention. As can be seen in FIG. 1, the hub assembly 10 includes a body 12 having a lumen 16 therethrough, and a seal 50 according to one embodiment of the present invention. The lumen 16 is sized to permit passage of a medical device 18 such as, for example, a therapy lead, guiding catheter, or a guide wire. The seal 50 is retained within the hub body 12, and is adapted to maintain a substantially positive fluid seal around the medical device 18 that is passed through the lumen 16. The hub 10 may be coupled to another medical device 51 such as a catheter or introducer sheath.

Figure 2A:
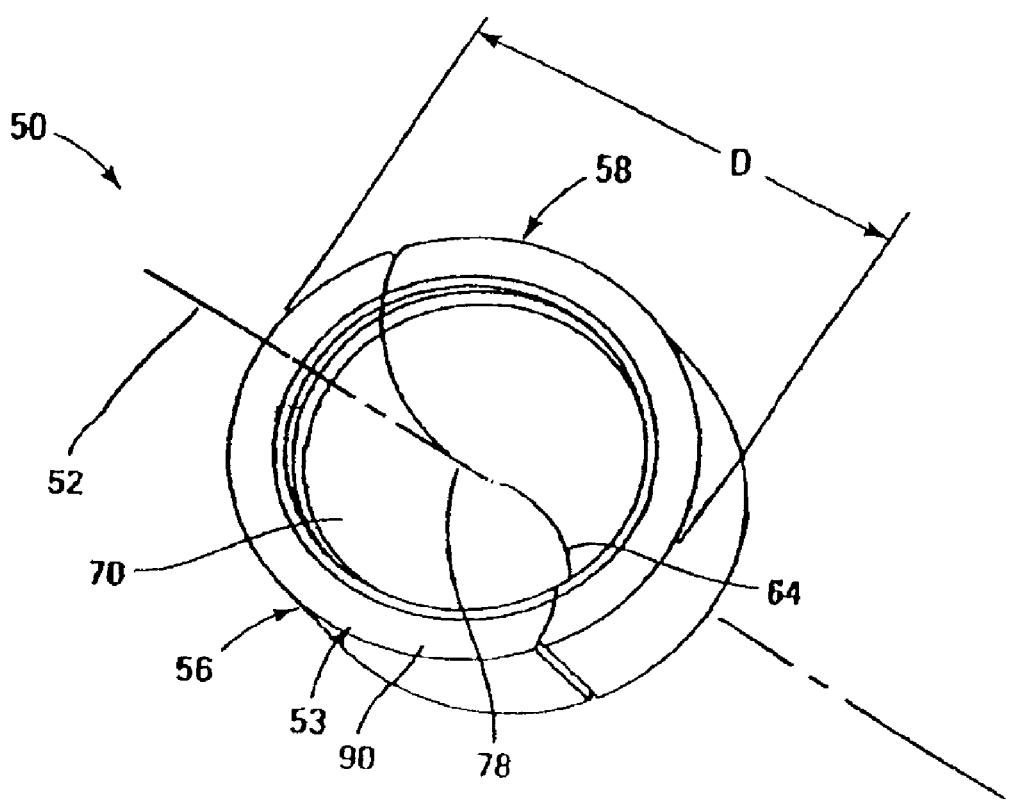
FIGS. 2A and 2B show proximal and distal perspective views of an assembled seal according to one embodiment of the present invention.
Figure 2B:
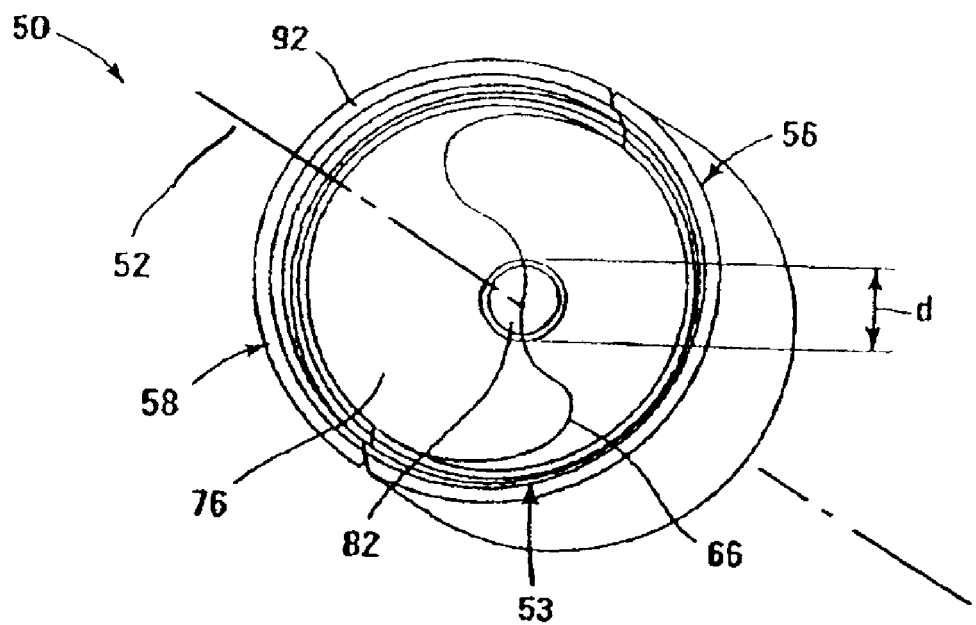

FIGS. 2A and 2B show proximal and distal perspective views of an assembled seal 50 according to one embodiment of the present invention. As shown in FIGS. 2A and 2B, the seal 50 is, in one embodiment, generally cylindrical with a longitudinal axis 52 and a perimeter 53, and is composed of a first seal portion 56 and a mating second seal portion 58. The seal portions 56 and 58 are substantially equivalent in overall size and join at a proximal joint 64 and a distal joint 66 to form a proximal entrance area 70 and a distal exit area 76. Because the seal 50, in one embodiment, is composed of two, separate seal elements, it is particularly adaptable for use in splittable or cuttable medical devices such as splittable hemostasis or bleedback control valves or splittable introducer sheaths. In one embodiment, the seal portions 56 and 58 may be attached at or near the seal perimeter using an attachment method that permits the seal 50 to be readily split or cut.

In general, the shape of the seal 50 will be dictated by the configuration and requirements of the hemostasis valve, hub, or introducer sheath into which the seal 50 is inserted. In one embodiment, the seal 50 is generally cylindrical with an outer diameter D of from about 0.250 inches to about 0.750 inches. In one embodiment, the diameter D is about 0.600 inches. In another embodiment, the diameter D is about 0.450 inches. Although FIGS. 2A and 2B depict a cylindrical seal 50, this is not a requirement. To the contrary, other shapes (e.g., rectangular, elliptical) are within the scope of the present invention.

In one embodiment, the seal 50 may be made of polyisoprene. In other embodiments, other resilient materials may be used to form the seal 50, including, without limitation, silicone, latex, neoprene, and other rubber-based compounds as will be understood by those of ordinary skill in the art.

In one embodiment, shown in FIGS. 2A and 2B, the proximal entrance area 70 is generally conical and has an apex 78 near the longitudinal axis 52, and the distal exit area 76 is concave and may include a generally circular planar portion 82 disposed about and generally perpendicular to the longitudinal axis 52. In one embodiment, the planar portion 82 has a diameter d of from about 0.030 inches to about 0.100 inches. In one embodiment, the planar portion 82 has a diameter d of about 0.070 inches. In another embodiment, the planar portion 82 has a diameter d of about 0.050 inches. In other embodiments, the planar portion 82 may have a non-circular shape (e.g., rectangular, elliptical)

In one embodiment, the planar portion 82 may be centered about the longitudinal axis 52 and, in turn, the apex 78 of the proximal entrance area 70. In another embodiment, either or both of the planar portion 82 and the apex 78 of the proximal entrance area 70 may be offset from the longitudinal axis 52.

The seal 50 may optionally include means for facilitating retention of the seal 50 within another medical device such as, for example, a hemostasis valve or an introducer sheath. Such means may include a proximal retaining ring 90 and/or a distal retaining ring 92.

Figure 3:
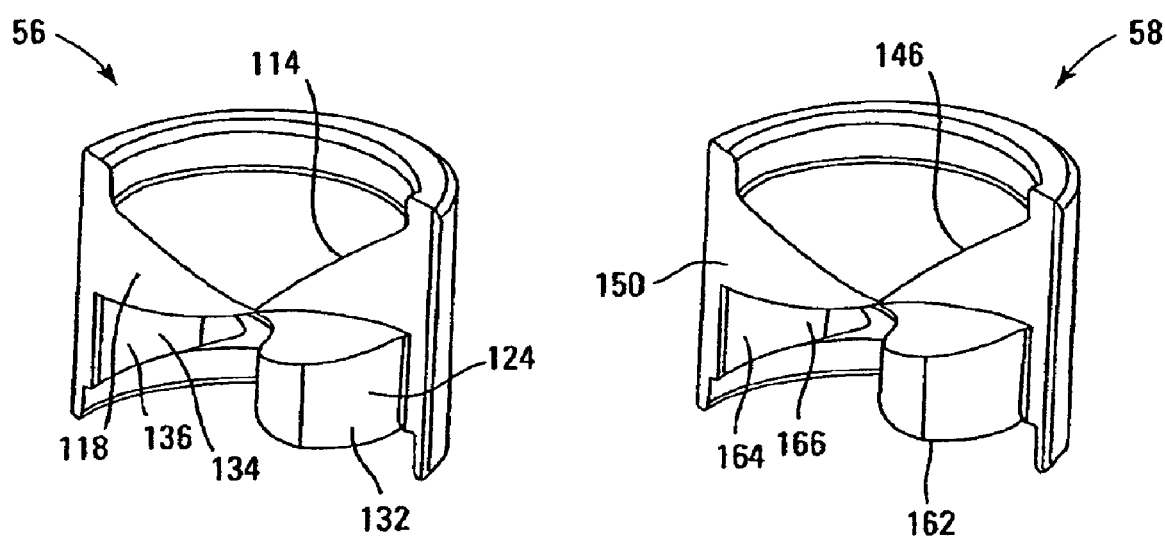
FIG. 3 shows perspective views of the mating first and second portions of the seal according to one embodiment of the present invention.
Figure 4:
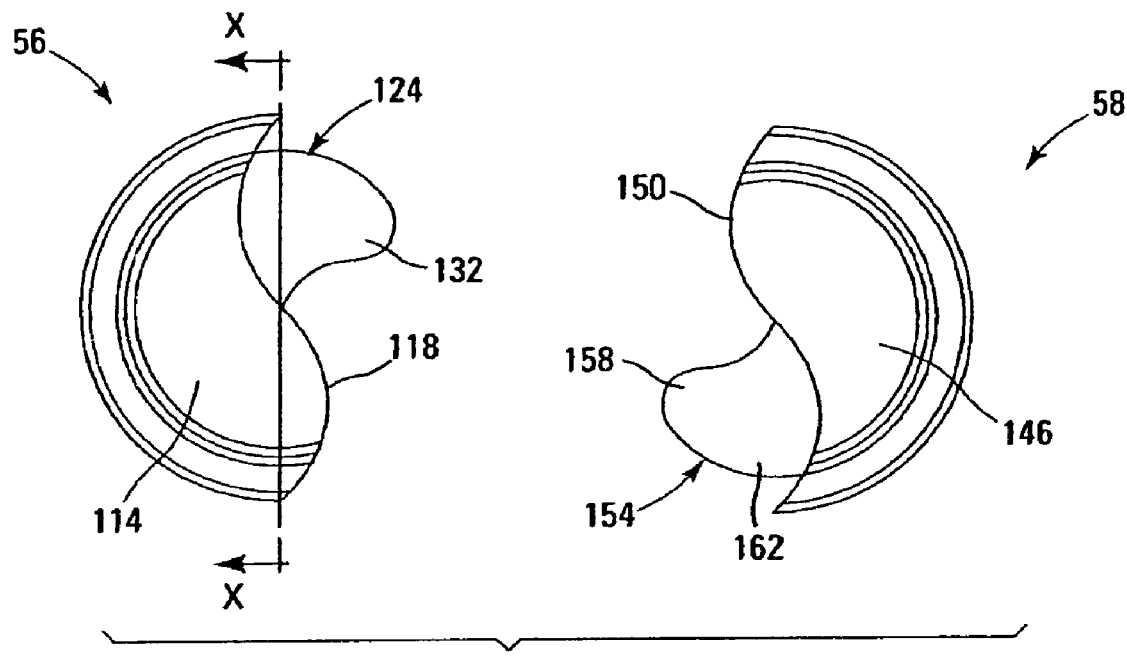
FIG. 4 shows the first and second seal portions from a proximal plan view, according to one embodiment of the present invention.
Figure 5:
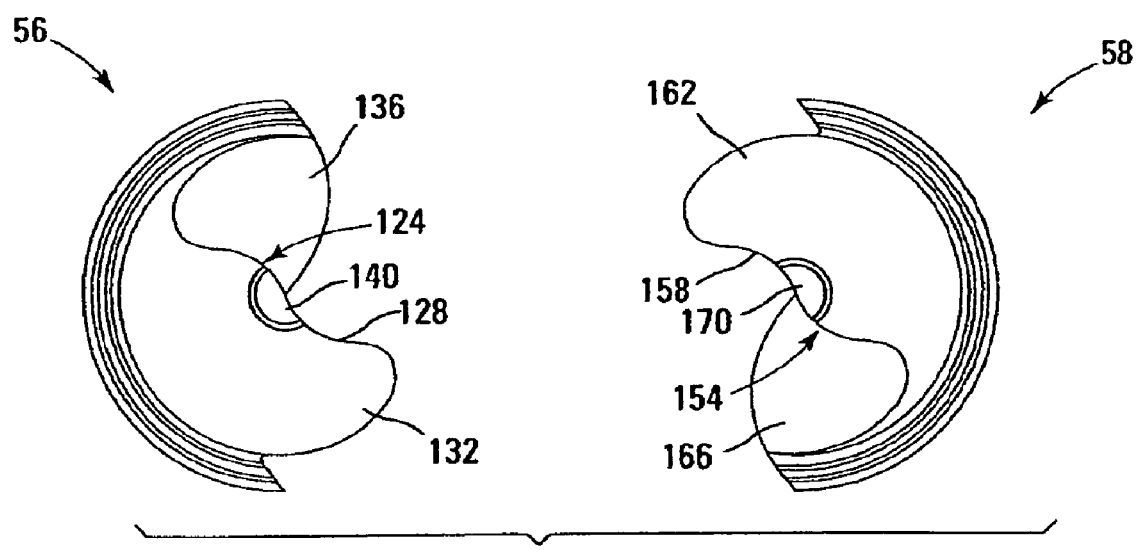
FIG. 5 shows the first and second seal portions from a distal plan view, according to one embodiment of the present invention.

FIG. 3 shows perspective views of the first and second seal portions 56 and 58, respectively. Additionally, FIGS. 4 and 5 are proximal (FIG. 4) and distal (FIG. 5) plan views of the seal portions 56 and 58. As shown in FIGS. 3, 4 and 5, the first seal portion 56 includes a first proximal sealing member 114 having a first mating surface 118, a first projection 132, a first distal wall 134 defining a first recess 136, and a first planar subportion 140. The second seal portion 58 includes a second proximal sealing member 146 having a second mating surface 150, a second projection 162, a second distal wall 164 defining a second recess 166, and a second planar subportion 170.

In one embodiment, the mating surfaces 118 and 150 are each contoured to generally form an 'S'-shape. Accordingly, in this embodiment, the proximal joint 64 in the assembled seal 50 is also 'S'-shaped (See FIG. 2A). In one embodiment, each half of the 'S' of the contoured mating surfaces 118 and 150 may have a radius of curvature of from about 0.125 inches to about 0.250 inches. In one embodiment, the radius of curvature is about 0.150 inches. In another embodiment, the radius of curvature is about 0.187 inches. In other embodiments, the mating surfaces 118 and 150 may be configured in other shapes. When the seal portions 56 and 58 are assembled to form the seal 50, the proximal sealing members 114 and 146 form the proximal entrance area 70 (See FIG. 2A).

In one embodiment, the projections 132 and 162 are generally sized and shaped to be inserted into and to sealingly mate with and engage the recesses 166 and 136, respectively, when the seal portions 56 and 58 are assembled to form the seal 50. When so engaged, the projections 132 and 162 generally form the distal exit area 76 (See FIG. 2B). In the assembled seal 50, the planar subportions 140 and 170 join to form the generally planar portion 82 (see FIG. 2B).

The recesses 136 and 166 are sized and shaped to receive the projections 132 and 162. In one embodiment, when the seal 50 is assembled, substantially all of the adjacent surfaces of the projections 132 and 162 and the recesses 166 and 136 are in sealing contact with one another.

In one embodiment, as shown in FIGS. 3, 4 and 5, the projections 132 and 162 and, accordingly, the recesses 136 and 166, are curved, although this is not a requirement of the present invention. In other embodiments, for example, the projections 132 and 162 may be substantially triangular or rectangular, and the recesses 166 and 136 are shaped to sealingly receive the projections.

As shown in FIGS. 4 and 5, in one embodiment, the first proximal sealing member 114 intersects the first projection 132, and the second proximal sealing member 146 intersects the second projection 162, at approximately 90 degree angles and at approximately the longitudinal axis 52. As a result, the proximal sealing members 114 and 146 overlap the distal joint 66 (see FIG. 2B), and the projections 132 and 162 overlap the proximal joint 64, at substantially all points other than the longitudinal axis 52. As discussed below, this results in sealing around substantially the entire circumferential surface of a medical device (e.g., a cardiac lead) that is inserted through the seal.

Figure 6:
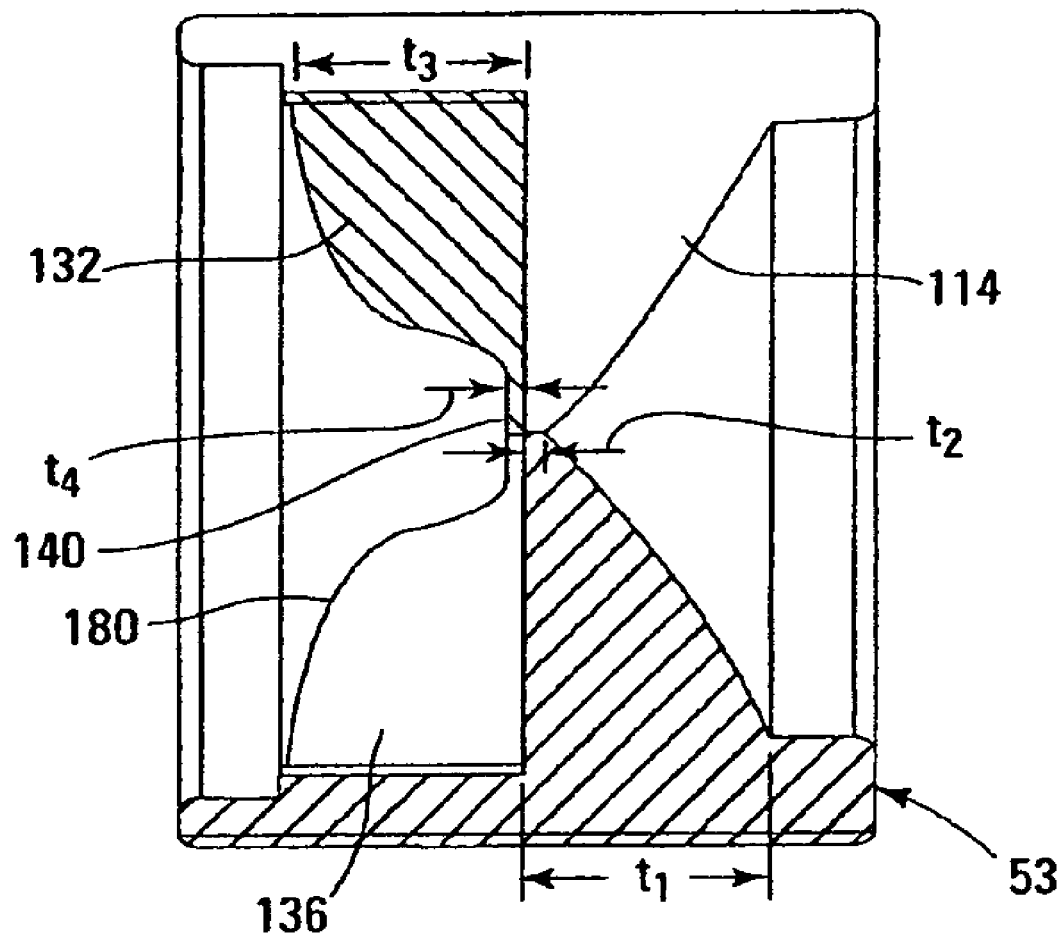
FIG. 6 is a partial cross-sectional view of the first seal portion according to one embodiment of the present invention.

FIG. 6 is a partial cross-sectional view of the first seal portion 56 taken along the line X-X in FIG. 4. It should be understood that, although not shown in FIG. 6, the features of the second seal portion 58 are generally configured to have the same size and shape as the corresponding features of the first seal portion 56. For example, the second proximal sealing member 146, the second projection 162, the second recess 166, and the second planar subportion 170 have generally the same dimensions and shape as the first proximal sealing member 114, the first projection 132, the first recess 136, and the first planar subportion 140, respectively.

Thus, as shown in FIG. 6, the proximal sealing members 114 and 146 are tapered radially inward, having a thickness t1 near the seal perimeter 53 and a thickness t2 near the apex 78. In one embodiment, the thickness t1 may range from about 0.075 inches to about 0.175 inches, and the thickness t2 may range from about 0.005 inches to about 0.025 inches. In one embodiment, the thickness t1 is about 0.125 inches and the thickness t2 is about 0.0075 inches.

As further shown in FIG. 6, the projections 132 and 162 are also thicker near the seal perimeter 53 than near the longitudinal axis 52, and transition into the planar subportions 140 and 170. In one embodiment, the projections 132 and 136 have a thickness t3 near the perimeter 53 that may range from about 0.075 inches to about 0.175 inches, and a thickness t4 of the planar subportions 140 and 170 of from about 0.005 inches to about 0.025 inches. In one embodiment, the thickness t3 is about 0.125 inches and the thickness t4 is about 0.0075 inches.

In the embodiment shown in FIG. 6, the projections 132 and 162 each have a contoured distal face 180, although in other embodiments, the projections 132 and 162 may have different shapes (e.g., concave) or may have a straight taper similar to the proximal sealing members 114 and 146.

In one embodiment, the thickness t2 of the proximal sealing members 114 and 146 near the apex 78 is thicker than the thickness t4 of the planar subportions 140 and 170. In one such exemplary embodiment, the thickness t2 is about 0.010 inches and the thickness t4 is about 0.005 inches.

Table 1 below shows the dimensions, in inches, discussed above for various exemplary embodiments of a seal 50 according to the present invention.

|   | D | d | t1 | t2 | t3 | t4 |
|---|---|---|----|----|----|----|
| 1 | 0.450 | 0.050 | 0.125 | 0.0075 | 0.125 | 0.0075 |
| 2 | 0.450 | 0.070 | 0.125 | 0.010 | 0.125 | 0.010 |
| 3 | 0.600 | 0.050 | 0.125 | 0.0075 | 0.125 | 0.0075 |
| 4 | 0.600 | 0.070 | 0.150 | 0.010 | 0.150 | 0.010 |
| 5 | 0.300 | 0.030 | 0.075 | 0.005 | 0.075 | 0.005 |
| 6 | 0.500 | 0.045 | 0.125 | 0.010 | 0.125 | 0.005 |
| 7 | 0.750 | 0.080 | 0.150 | 0.015 | 0.150 | 0.010 |
| 8 | 0.750 | 0.100 | 0.175 | 0.025 | 0.175 | 0.025 |

Figure 7:
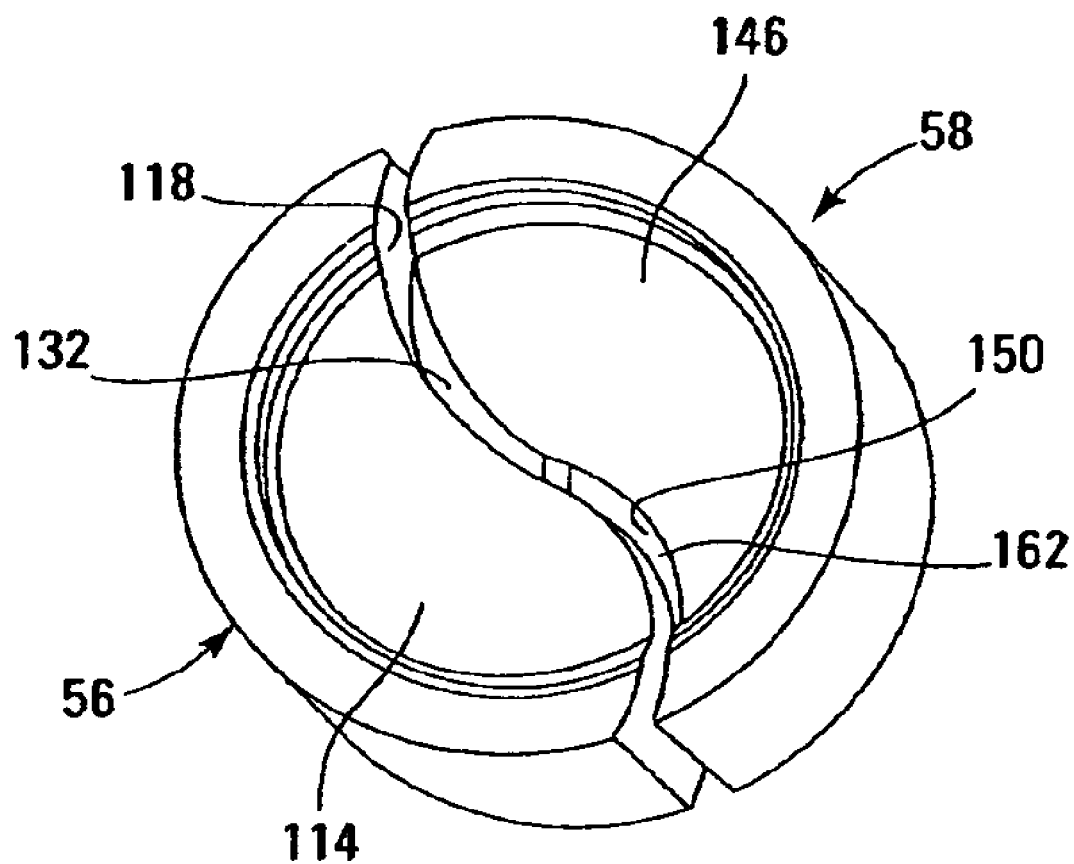
FIG. 7 is a perspective view of the seal according to one embodiment of the present invention, showing the seal portions partially separated.

FIG. 7 is a perspective view of the seal 50 according to one embodiment of the present invention, showing the seal portions 56 and 58 partially separated to show how the projections 132 and 162 effectively interlock.

Figure 8:
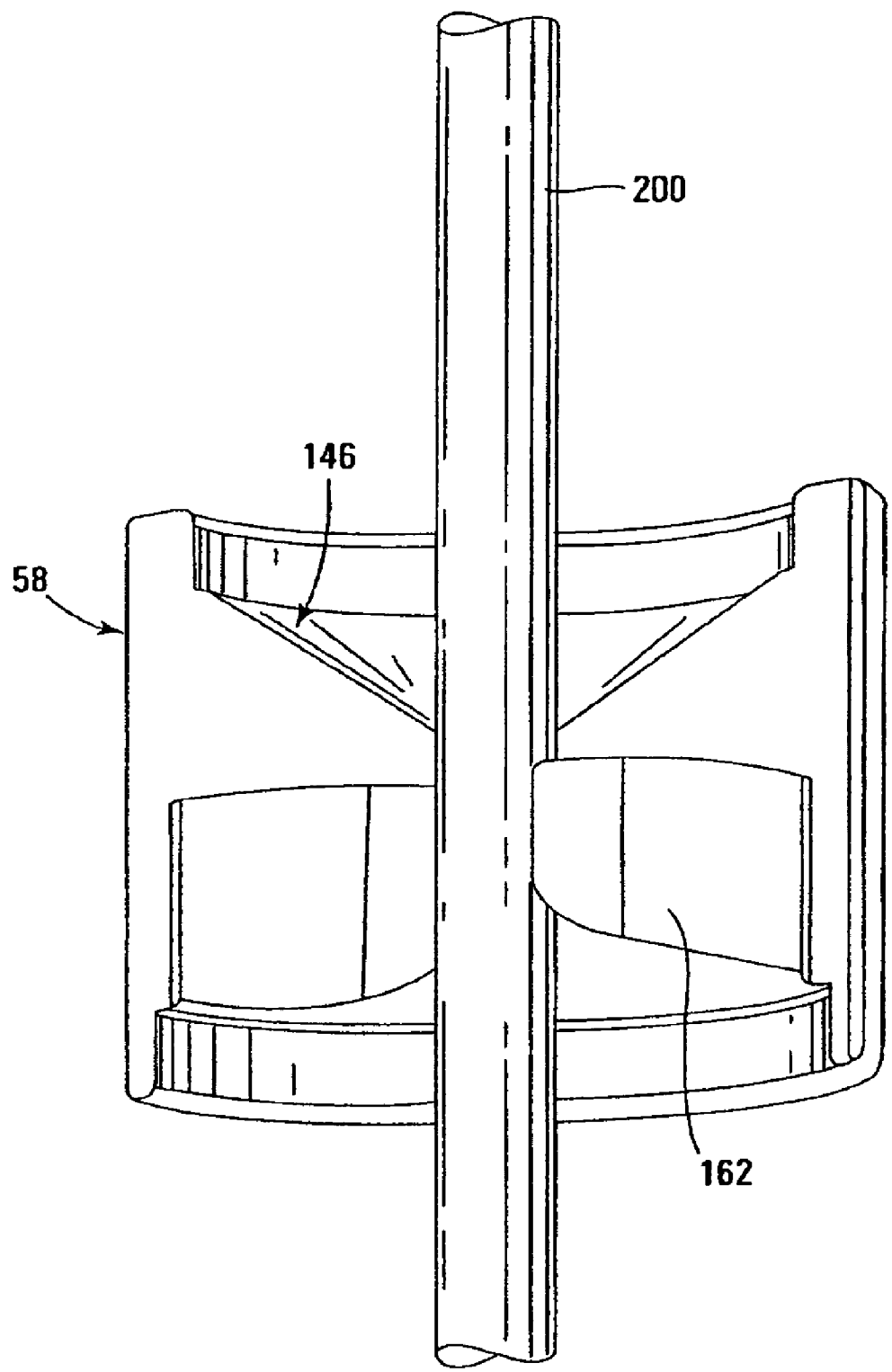
FIG. 8 is a partial perspective view of the seal according to one embodiment of the present invention with a medical device passing therethrough.
Figure 9:
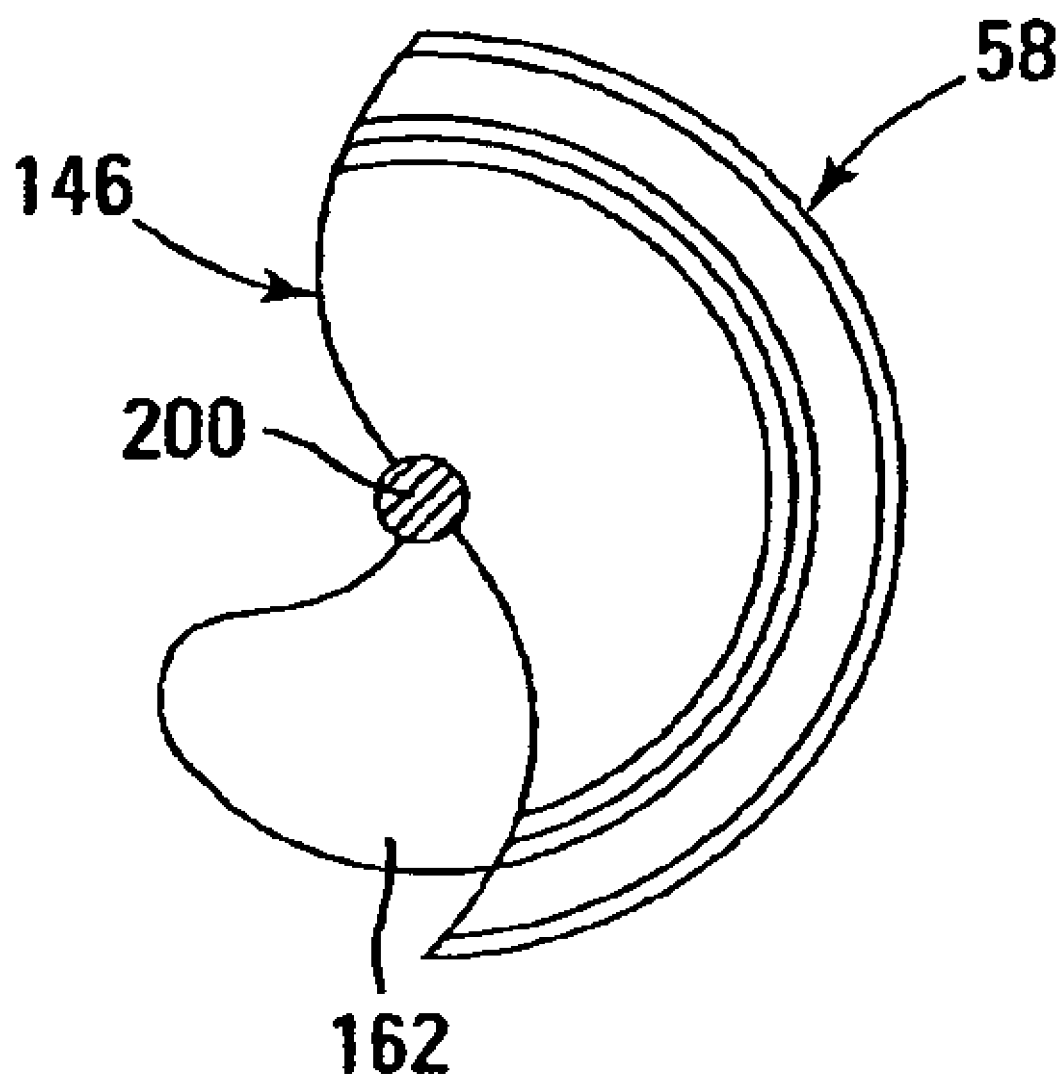
FIG. 9 is a partial proximal plan view of the seal, according to one embodiment of the present invention, with a medical device, such as a therapy lead, passing therethrough.

FIG. 8 is a partial perspective view, and FIG. 9 is a partial proximal plan view, of the seal 50 according to one embodiment of the present invention, with a medical device, such as a therapy lead 200, passing therethrough. For clarity, only the second seal portion 58 is shown in FIGS. 8 and 9. Exemplary medical devices that may be accommodated by the seal 50 according to one embodiment of the present invention include, without limitation, guide wires, therapy leads, and guide catheters, with outer diameters ranging from about 0.010 inches to about 0.170 inches. As will be apparent to those of ordinary skill in the art, the foregoing types of medical devices and the corresponding ranges of diameters are merely exemplary, and the seal 50 of the present invention may be adapted to accommodate larger or smaller diameter medical devices as may be required for a particular procedure.

As shown in FIGS. 8 and 9, the proximal sealing members 114 and 146 and the projections 132 and 162 interact to substantially fully encapsulate the lead 200 as it is passed between the seal portions 56 and 58. The contoured shape of the mating surfaces 118 and 150 tends to cause the proximal sealing members 114 and 146 to wrap around the lead 200. Similarly, in one embodiment, the projections 132 and 162 tend to wrap around the lead 200 as it passes through the seal 50. Working together, the proximal sealing members 114 and 146 and projections 132 and 162 substantially fully encapsulate a generally cylindrical medical device that is passed between the seal portions 56 and 58.

Additionally, the orientation of the mating surfaces 118 and 150 to the projections 132 and 162 result in at least the proximal sealing members 114 and 146, or the projections 132 and 162, being in sealing contact with the medical device 200 around the entire surface of the device. With a seal lacking projections 132 and 162, insertion of a medical device between the seal elements would result in leakage at points approximately 180 degrees apart where the two seal member join. As is apparent in FIGS. 4-7, however, the projections 132 and 162 overlap the proximal joint 64 at all points other than the longitudinal axis 52 and accordingly, in one embodiment, the apex 78, which is the point of entry of the medical device through the seal 50. Thus, the projections 132 and 162 seal around the medical device immediately distal to any areas of separation that may occur in the proximal joint 64. Similarly, the proximal sealing members 114 and 146 overlap the distal joint 66 at all points other than the apex 78. This has the resulting effect of sealing around the regions on the medical device proximal of the points of corner separation in the distal joint 66. Thus, the inserted medical device, the overlapping proximal sealing members 114 and 146, and the projections 132 and 162 interact to eliminate any pathways for leakage of bodily fluids through the seal 50.

The projections 132 and 162 also operate to stabilize and hold the seal portions 56 and 58 in alignment when the lead 200 or other medical device is inserted through the seal 50. A seal without such projections may tend to become misaligned due to, for example, relative translation of the two separate seal components along their joint line, when a device is inserted into or removed from the seal. In the present invention, however, according to one embodiment, the walls 128 and 158 in the recesses 136 and 166 restrict displacement of the projections 132 and 162, respectively. This in turn restricts relative movement of the seal portions 56 and 58. In addition, the interlocking design of the projections 132 and 162 and the recesses 136 and 166, respectively, similarly restricts rotational movement of the seal elements 70 and 76 relative to each other.

The stabilizing effect of the projections 132 and 162 is further promoted by their profiles. Near the longitudinal axis 52, the projections 132 and 162 are relatively thin, which promotes effective sealing while at the same time reduces resistance to movement of the lead 200 or other medical device through the seal 50. This provides a beneficial combination of effective sealing without unduly restricting the travel of the medical device through the seal 50. At the same time, the thicker portions of the projections 132 and 162 near the perimeter of the seal 50 beneficially stiffens the projections which further inhibits misalignment of the seal portions 56 and 58.

In addition, the geometry of the seal 50 advantageously promotes centering the medical device, such as the lead 200, as it is passed through the seal 50. The orientation of the projections 132 and 162 at approximately 90 degrees relative to the proximal joint 64 inhibits the lead 200 from sliding along the proximal joint 64, as would tend to occur if the projections 132 and 162 were not present. Accordingly, the projections 132 and 162 operate to maintain the lead 200 or other medical device at a position at or near the longitudinal axis 52 (see FIG. 2A).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A hemostasis seal configured to permit passage of a medical device therethrough, the seal comprising:
   a first resilient seal portion including a first sealing member having a first mating surface, a first projecting portion, and a first receiving portion defining a first recess; and
   a second resilient seal portion including a second sealing member having a second mating surface, a second projecting portion, and a second receiving portion defining a second recess,
   wherein the seal is cylindrical with a perimeter and a longitudinal axis, and
   wherein the first and second sealing members each have a first thickness near the seal perimeter and a second thickness near the longitudinal axis, wherein the first thickness is greater than the second thickness, and the first and second projecting portions each have a third thickness near the seal perimeter and a fourth thickness near the longitudinal axis, wherein the third thickness is greater than the fourth thickness, and
   wherein the first mating surface mates with the second mating surface to form a first fluid seal, and
   wherein the first and second projecting portions mate with and are sealingly received by the second and first recesses of the second and first receiving portions, respectively, to form a second fluid seal, and
   wherein at least a portion of each of the first projecting portion and the second projecting portion is adapted to contact the medical device when the medical device is passed between the first and second seal portions.

2. The seal of claim 1 wherein the third thickness is about 0.125 inches and the fourth thickness is about 0.0075 inches.

3. The seal of claim 1 wherein the third thickness is about 0.150 inches and the fourth thickness is about 0.010 inches.

4. The seal of claim 1 wherein the projecting portions interlock to form the second fluid seal with respect to the medical device.

5. The seal of claim 1 wherein the first and second mating surfaces are generally 'S'-shaped.

6. The seal of claim 1 wherein the first projecting portion is oriented generally perpendicular to the first mating surface near the longitudinal axis, and wherein the second projecting portion is oriented generally perpendicular to the second mating surface near the longitudinal axis.

7. A hemostasis seal configured to permit passage of a medical device therethrough, the seal being cylindrical with a perimeter and a longitudinal axis and comprising:
   a first resilient seal portion including a first mating surface and a projecting portion; and
   a second resilient seal portion including a second mating surface adapted to mate with the first mating surface, and a receiving portion defining a recess that sealingly receives and mates with the projecting portion,
   wherein the first and second seal portions each include a proximal sealing member having a first thickness near the perimeter and a second thickness near the longitudinal axis, and wherein the first thickness is greater than the second thickness, and
   wherein the projecting portion has a third thickness near the seal perimeter and a fourth thickness near the longitudinal axis, and wherein the third thickness is greater than the fourth thickness, and
   wherein at least a portion of each of the first and second mating surfaces and the projecting and receiving portions is configured to contact the medical device, such that the seal is configured to sealingly engage the medical device about substantially an entire circumferential surface thereof when the medical device is passed between the first and second seal portions.

8. The seal of claim 7 wherein the seal is cylindrical with a perimeter and a longitudinal axis, and wherein the seal further comprises a proximal sealing member having a first thickness of from about 0.075 inches to about 0.175 inches near the seal perimeter and a second thickness of from about 0.005 inches to about 0.025 inches near the longitudinal axis, and wherein the projecting portion has a third thickness of from about 0.075 inches to about 0.175 inches near the seal perimeter and a fourth thickness of from about 0.005 inches to about 0.025 inches near the longitudinal axis.

9. The seal of claim 8 wherein the first thickness is about 0.125 inches, the second thickness is about 0.0075 inches, the third thickness is about 0.125 inches, and the fourth thickness is about 0.0075 inches.

10. The seal of claim 7 wherein the projecting portion is oriented generally perpendicular to the first mating surface near the longitudinal axis.

11. A hemostasis seal configured to permit passage of a medical device therethrough, the seal comprising:
    a first resilient seal portion including a first proximal sealing member, a first mating surface and a projecting portion; and
    a second resilient seal portion including a second proximal sealing member, a second mating surface adapted to mate with the first mating surface, and a receiving portion adapted to generally mate with the projecting portion,
    wherein the seal is cylindrical with a perimeter and a longitudinal axis, and wherein each of the proximal sealing members has a first thickness near the perimeter and a second thickness near the longitudinal axis, the first thickness being greater than the second thickness, and
    wherein the projecting portion has a third thickness near the seal perimeter and a fourth thickness near the longitudinal axis, the third thickness being greater than the fourth thickness, and
    wherein the seal is configured to sealingly engage the medical device about substantially an entire circumferential surface thereof when the medical device is passed between the first and second seal portions.

12. The seal of claim 11 wherein the first thickness is from about 0.075 inches to about 0.175 inches, the second thickness is from about 0.005 inches to about 0.025 inches, the third thickness is from about 0.075 inches to about 0.175 inches, and the fourth thickness is from about 0.005 inches to about 0.025.

13. The seal of claim 12 wherein the first thickness is about 0.125 inches, the second thickness is about 0.0075 inches, the third thickness is about 0.125 inches, and the fourth thickness is about 0.0075 inches.

14. The seal of claim 11 wherein the first and second projecting portions interlock to form the second fluid seal with respect to the medical device.

15. The seal of claim 11 wherein the first and second mating surfaces are generally 'S'-shaped.

* * * * *